US010765848B2

(12) United States Patent
Dimino et al.

(10) Patent No.: US 10,765,848 B2
(45) Date of Patent: Sep. 8, 2020

(54) DEVICE AND FORMULATION FOR TOPICAL TREATMENT OF PAIN AFFECTING THE VULVAR AREA OF THE FEMALE HUMAN GENITAL ORGAN

(71) Applicant: Gruenenthal GmbH, Aachen (DE)

(72) Inventors: Andre Dimino, Woodcliff Lake, NJ (US); Marco Pappagallo, New York, NY (US); Michael Richardson, NY Wayne, PA (US); Franz Gerstheimer, Aachen (DE); Emilio Garcia Quetglas, Cabanillas del Campo Guadalajara (ES); Jacqueline Delfgaauw, Jersey City, NJ (US); Andreas Scholz, Giessen (DE); Johannes Niel Van, Volkel (NL)

(73) Assignee: GRUENENTHAL GMBH, Aachen (DE)

( * ) Notice: Subject to any disclaimer, the term of this patent is extended or adjusted under 35 U.S.C. 154(b) by 519 days.

(21) Appl. No.: 15/351,036

(22) Filed: Nov. 14, 2016

(65) Prior Publication Data
US 2017/0056635 A1 Mar. 2, 2017

Related U.S. Application Data

(63) Continuation of application No. PCT/EP2015/000989, filed on May 13, 2015.
(Continued)

(51) Int. Cl.
*A61K 9/00* (2006.01)
*A61L 15/44* (2006.01)
*A61M 31/00* (2006.01)

(52) U.S. Cl.
CPC .......... *A61M 31/00* (2013.01); *A61K 9/0014* (2013.01); *A61K 9/0034* (2013.01); *A61L 15/44* (2013.01);
(Continued)

(58) Field of Classification Search
CPC .......... A61L 15/44; A61L 15/18; A61L 15/34; A61L 15/40; A61L 15/46;
(Continued)

(56) References Cited

U.S. PATENT DOCUMENTS 3,521,637 A 7/1970 Waterbury
3,902,493 A 9/1975 Baier et al.
(Continued)

FOREIGN PATENT DOCUMENTS

EP 1 782 831 A1 5/2007
WO WO 99/47121 A1 9/1999
(Continued)

OTHER PUBLICATIONS

International Search Report (PCT/ISA/220 & PCT/ISA/210) issued in PCT Application No. PCT/EP2015/000989 dated Oct. 1, 2015 (seven pages).
(Continued)

Primary Examiner — Tatyana Zalukaeva
Assistant Examiner — Gabriella E Burnette
(74) Attorney, Agent, or Firm — Norris McLaughlin, P.A.

(57) ABSTRACT

The present invention relates to a device for the topical treatment of pain affecting the vulvar area of the female human genital organ, a formulation for use in the device according to the invention, and a kit comprising the device according to the present intention. Additionally, the present invention relates to a method of topical treatment of pain affecting the vulvar area of the female human genital organ, said method using the device according to the present invention. The device is a layered article shaped to be placed in use inside a female undergarment and at least partially in skin contact with the female vulvar area and comprises a topical formulation.

6 Claims, 3 Drawing Sheets

Related U.S. Application Data

(60) Provisional application No. 61/993,675, filed on May 15, 2014.

(52) U.S. Cl.
CPC ... *A61L 2300/102* (2013.01); *A61L 2300/432* (2013.01); *A61M 2210/14* (2013.01)

(58) Field of Classification Search
CPC .......... A61L 2300/102; A61L 2300/30; A61L 2300/404; A61L 2300/432; A61F 13/15; A61F 13/51113; A61F 13/51117; A61F 2015/51117; A61F 13/20; A61M 35/00; A61M 2210/14; A61M 31/00
See application file for complete search history.

(56) References Cited

U.S. PATENT DOCUMENTS

| | | | | |
|---|---|---|---|---|
| 5,178,139 | A * | 1/1993 | Angelillo | A61F 7/03 604/358 |
| 6,150,400 | A * | 11/2000 | Nyirjesy | A61K 31/00 514/456 |
| 6,355,637 | B1 * | 3/2002 | Axt | C07D 239/90 514/234.5 |
| 6,468,557 | B1 | 10/2002 | Lezdey et al. | |
| 8,178,746 | B2 * | 5/2012 | Hildeberg | A61F 5/441 604/359 |
| 2003/0100877 | A1 * | 5/2003 | Erdman | A61F 13/15577 604/385.23 |
| 2003/0120225 | A1 * | 6/2003 | Everhart | A61F 13/47209 604/285 |
| 2005/0095232 | A1 | 5/2005 | Volkmann | |
| 2010/0030172 | A1 * | 2/2010 | Husmark | A61F 13/15 604/360 |

FOREIGN PATENT DOCUMENTS

| | | |
|---|---|---|
| WO | WO 00/69483 A1 | 11/2000 |
| WO | WO 02/102424 A1 | 12/2002 |
| WO | WO 03/045412 A1 | 6/2003 |
| WO | WO 2006/014693 A1 | 2/2006 |
| WO | WO 2008/110872 A2 | 9/2008 |
| WO | WO 2013/175322 A1 | 11/2013 |

OTHER PUBLICATIONS

Written Opinion (PCT/ISA/237) issued in PCT Application No. PCT/EP2015/000989 dated Oct. 1, 2015 (nine pages).
Cover page of EP 1 448 212 A1 published Aug. 25, 2004 (one page).
Cover page of EP 1 178 846 A1 published Feb. 13, 2002 (one page).
Amin et al.; "Evaluation of Effect of Non Steroidal Anti-Inflammatory Drugs on Growth of Probiotics"; Int. J. Pure Appl. Sci. Technol., 20(1) (2014), pp. 25-35.

* cited by examiner

DEVICE AND FORMULATION FOR TOPICAL TREATMENT OF PAIN AFFECTING THE VULVAR AREA OF THE FEMALE HUMAN GENITAL ORGAN

The present invention relates to a device for the topical treatment of pain affecting the vulvar area of the female human genital organ, a formulation for use in the device according to the invention, and a kit comprising the device according to the present intention. Additionally, the present invention relates to a method of topical treatment of pain affecting the vulvar area of the female human genital organ, said method using the device according to the present invention.

Vulvodynia is a chronic pain syndrome that affects the vulvar area of the female human genital organ. It occurs primarily without identifiable cause or visible pathology. The condition can be mild to severe and can manifest in a specific area of the vulva or its entirety, however there has been reported a higher prevalence of the condition in the vestibule area of the vulva, referred to as vulvar vestibulitis syndrome (VVS). Although there is no known cure for vulvodynia, typical treatment is multidisciplinary and includes, among other treatment methods and modalities, the use of topically applied ointments, creams, gels and moisturizers for lubrication and soothing effects as well as the use of topical analgesic, anesthetic, anti-inflammatory and hormonal medications to block, reduce or eliminate the pain. WO 2008/110872 for instance describes foamable compositions containing a combination of a sodium channel agent, a cholinergic agent and a nitric oxide donor. Vulvodynia is mentioned in this reference as one of numerous conditions for the treatment of which the foamable compositions are considered suitable. The current method for applying the foregoing topical agents to the treatment area is placing an amount of the topical agent on the hand and then spreading the agent on the surface of the skin of the vulvar area where the pain radiates. This method is inefficient and non-hygienic and awkward for the patient to practice during daily business, necessitating the availability of locations offering sufficient privacy to carry out the application.

The application of medication directly to the surface skin area of the female human genital organ has already been suggested for quite some time now. It has for instance been suggested to use disposable absorbent articles such as sanitary napkins, panty liners, intralabial absorbent devices or tampons to administer pharmaceutical substances.

WO 99/47121 proposes the administration of therapeutic agents by using disposable absorbent articles, such as tampons, but neither teaches any device specifically adapted for such an administration, nor does it give any information as to which pharmaceutical compound might be used or which medical condition might be treated using such absorbent devices.

WO 02/102424 describes disposable absorbent articles such as sanitary napkins, panty liners and interlabial menstruation protection device adapted for the treatment and/or prevention of the pre-menstrual syndrome. To achieve systemic administration of a pharmaceutical substance suitable for the treatment of the pre-menstrual syndrome, it is suggested to cover conventional absorbent articles at least partially by a transdermal therapeutic system suitable for delivering the active agent to the body.

U.S. 2005095232A1 proposes a vaginal care composition for the protection of the mucosa of the vagina, said composition comprising selected viable or non-viable bacteria/microorganisms. Among other methods of administration of such a care composition, it is suggested to do so via the incorporation of the care composition into a tampon or a panty liner. Similarly, U.S. Pat. No. 3,521,637 proposes a tampon or sanitary napkin which contains vitamin A for the treatment and/or prevention of assorted diseases related to infections of the vagina. Vitamin A is incorporated into the absorbent article either in microencapsulated form within the fibrous matrix of the tampon/sanitary napkin or enclosed within one or more rupturable membranes or capsules within such a matrix. Similarly, U.S. Pat. No. 3,902,493 describes a medicated catamenial tampon for control and treatment of vaginal area disorders such as vaginitis. The tampon comprises a resilient foam corpus and a medicament bearing hydrophobic non-woven overwrap which is permeable to catamenial fluids, and is adapted for non-menstrual as well as menstrual delivery of medicament to control and treat vaginal area disorders.

The above discussed devices either suggest the use of conventional absorbent articles for the delivery of pharmaceutical agent via or to the skin surface of the human female genital organ or propose the use of specifically adapted tampons for this purpose. None of these devices are suggested for the treatment pain in vulvar area of the human female body.

There remains a need for a device specifically designed for the topical treatment of pain in the vulvar area of the female human genital organ.

Accordingly, it is the object of the present invention to provide a device for the topical treatment of pain affecting the vulvar area of the female human genital organ. It is furthermore an object of the present invention to provide a method for the topical treatment of pain affecting the vulvar area of the female human genital organ.

In a first aspect of the present invention, a device for the topical treatment of pain affecting the vulvar area of the female human genital organ is provided, wherein the device is a layered article shaped to be placed in use inside a female undergarment and at least partially in skin contact with the female vulvar area, said article having a longitudinal direction, a transverse direction, a front end, a back end, and two longitudinal sides, and said device comprises at least
  a) a formulation-impermeable outer layer having an outer surface and an inner surface;
  b) a carrier layer having an inner carrier surface and a skin-contacting surface, wherein said inner carrier surface faces in the direction of the inner surface of the formulation-impermeable outer layer; and
  c) a fluid topical formulation comprising at least one active agent for treating pain affecting the vulvar area of the female human genital organ.

In one embodiment of the device according to the invention, the carrier layer is at least partially impregnated with the fluid topical formulation.

In a second aspect of the present invention, a device for the topical treatment of pain affecting the vulvar area of the female human genital organ is provided, wherein the device is a layered article shaped to be placed in use inside a female undergarment and at least partially in skin contact with the female vulvar area, said article having a longitudinal direction, a transverse direction, a front end, a back end, and two longitudinal sides, and said device comprises at least
  a) a formulation-impermeable outer layer having an outer surface and an inner surface;
  b) a formulation-impermeable rim layer, wherein said rim layer is superimposed on the inner surface of formulation-impermeable outer layer and does not cover an inner section thereof thereby defining a channel extending in the longitudinal direction of the article;

c) a carrier layer having an inner carrier surface and a skin-contacting surface, said carrier layer being superimposed on the formulation-impermeable rim layer and the channel such that the inner carrier surface faces in direction of the formulation-impermeable rim layer and the channel;

wherein the carrier layer is at least partially impregnated with a topical formulation and/or at least one dispensing unit is positioned interposed between the formulation-impermeable outer layer and the formulation-impermeable rim layer adjacent to the channel and said dispensing unit contains a topical formulation to be released into the channel.

The device according to the present invention enables the easy, efficient and hygienic topical application of the pain-relieving active agent to the affected skin area. The shape of the device is of such a form that the device can be placed inside the undergarment of the patient, i.e. the device is shaped to essentially conform to the female anatomy in the genital area when in use. Consequently, the article may be of essentially elongated shape covering the vulvar area. Examples of such shapes are those commonly used for disposable personal hygiene articles, such as sanitary napkins or panty liners used by women especially during menstruation.

The device is simply placed inside the patient's undergarment just like a conventional absorbent article such as a sanitary napkin or panty liner, whereby the carrier layer faces in the direction of the skin of the patient. During use, the skin-contacting surface of the carrier layer is brought into contact with the patient's skin in the affected skin area causing the topical formulation, which is impregnated on the carrier layer or released from the dispensing unit into the channel and thereby to the carrier layer, to be administered to the patient's skin. In those embodiments of the invention, in which a dispensing unit is included, the channel defines the area of the device to which topical formulation is released by the dispensing unit to the carrier layer. The channel can be shaped to maximize distribution of topical formulation to selected areas of the carrier layer. It is apparent that the topical application of the formulation will be most effective when the channel has a shape that enables administration of the topical agent to the skin of the patient in those areas most affected by the pain condition.

The provision of a dispensing unit in the article according to the invention combines several advantages. For one thing, the topical formulation can be confined within the dispensing unit prior to use of the article, which has advantages with regard to the manufacturing, packaging and subsequent handling of the device. Additionally, the dispensing unit can be designed to enable facile sequential dosing of topical formulation by the patient during use of the article. This enables an on-demand provision of active agent to the patient, which is especially helpful as the pain caused by vulvodynia is of a chronic nature and often varies in intensity over time. The dispensing unit can for instance be pressure-activated and additional topical formulation can be released form the unit into the channel via exertion of pressure on the dispensing unit whilst the device is in use, e.g. simply by pressing on the reservoir with a finger. This has the advantage that the patient need not remove her garments to receive an additional dose of topical formulation, making sequential dosing much easier and less awkward during daily activities.

The formulation-impermeable outer layer can be made of any operative material that is or has been treated to render it essentially impermeable to the topical formulation. It can for instance be made of any one of the materials that are conventionally used as so called "back-sheets" in sanitary napkins or panty liners, provided the material provides a sufficient impermeability with respect to the topical formulation to prevent leakage of topical formulation onto the undergarment. The formulation-impermeable outer layer may be selected from materials comprising polymeric films, woven fabrics or non-woven fabrics, as well as combinations and composites thereof. For instance, the formulation-impermeable outer layer may include a polymeric film laminated to a woven or non-woven fabric. Suitable polymeric film materials can for instance be composed of polyethylene, polypropylene, polyester, polyvinyl chloride, nylon or the like, as well as combinations thereof. Suitably, the formulation-impermeable outer layer is made of a breathable material, e.g. a microporous film material that in use permits sufficient passage of air and moisture through the article, but blocks the passage of the topical formulation. If a woven or non-woven fabric or combinations thereof are used as the formulation-impermeable outer layer, a least one of these layers must have been treated to render it operatively impermeable to the topical formulation. Another suitable material for use as or in the formulation-impermeable outer layer is closed-cell polyolefin foam. Typically, the formulation-impermeable outer layer can be a back-sheet made of low density polyethylene ("LDPE") or biaxially oriented polypropylene ("BOPP"). Such liquid impermeable materials are well known for instance in the art of disposable articles and readily commercially available. Besides impermeability to the topical formulation the material used should be sufficiently flexible to enable the device to conform to the anatomy of the user. Preferably, the material has a surface energy that allows the adhesion of pressure sensitive adhesives, and preferably, the material is printable. Consequently, in embodiments of the present invention, the formulation-impermeable outer layer comprises a first formulation-impermeable material selected from the group consisting of non-porous materials, porous materials rendered liquid impermeable, microporous materials and closed cell foams or combinations thereof.

The outer surface of the formulation-impermeable outer layer may be treated to enhance wearing comfort. Suitable treatments to enhance the properties of such surfaces are for instance described in WO 2013/175322. Alternatively or additionally, a layer of material providing a softer feel to the skin can be provided as part of a laminated composite material used as the formulation-impermeable outer layer.

Optionally, the formulation-impermeable outer layer can be micro-embossed, have a printed design or can have a printed message to the consumer on its outer surface, or the layer can be at least partially colored.

The material used for the formulation-impermeable rim layer should be sufficiently flexible to allow the device in use to conform to the anatomy of the user and should be suitable to be bonded to the adjacent material layers via an adhesive, e.g. the material should exhibit suitable surface energy required for the use of adhesives. The materials used for the formulation-impermeable rim layer can for instance be chosen from the same materials that can be used for the formulation-impermeable outer layer.

The carrier layer is made of a porous or semi-porous material that allows impregnation and/or the absorption of the topical formulation onto the material of the carrier layer and thereby the delivery of the topical formulation to the treatment area. If no dispensing unit is included in the device, the material must be able to absorb a predetermined amount of the topical formulation to store it in the carrier layer in a controlled manner until use and must be able to release at least part of the topical formulation to the skin surface of the treatment area once the device is brought into position for use. In respect with the term "carrier layer" the word "impregnated" is to be understood in the sense that the porous or semi-porous material of the carrier layer has been brought into contact with an amount of topical formulation and that at least part of the amount of the topical formulation is absorbed by the material forming the carrier layer, e.g. via absorption into the layer due to capillary forces related to the porous or semi-porous nature of the material. Suitable materials include porous or semi-porous materials made of cotton, paper or cellulosic materials. Consequently, in further embodiments of the invention, the carrier layer comprises a porous or semi-porous material selected from the group of polymeric materials, cotton, paper or cellulosic materials. Such porous or semi-porous materials include woven, non-woven or foamed materials, for instance open-cell foamed materials. Examples of such materials are a spunbond polymeric non-woven materials, e.g. spunbond, nonwoven fabrics made of high density polyethylene, such as Tyvek©, available from the company DuPont, hygiene product polymeric non-woven materials such as those available from the Polymer Group, Inc., or for instance cotton batting non-woven materials, e.g. a full cotton batting non-woven with for instance 3 mm thickness. Absorption of the topical formulation into the carrier layer is driven by wicking action due to the porous nature of the material. In some embodiments the material from which the carrier layer is made has a preferred direction of transport of liquid formulation within the material, especially in the direction perpendicular to the outer surface of the carrier layer. This facilitates the containment of the topical formulation essentially in predetermined areas of the topical carrier layer, i.e. in those areas brought directly into contact with the topical formulation for absorption thereof. Such materials are for instance known from their use in hygiene-products, such as diapers, sanitary napkins etc. If a dispensing unit is provided in the device, the porous carrier material should be able to efficiently transport the topical formulation that is dispensed into the channel to the skin-contacting surface of the carrier layer so that the topical formulation can be brought into contact with the skin surface in the treatment area. Again, if the material is designed to exhibit a preferred direction of transport for liquid materials, this will be advantageous to maximize the transport of topical formulation to the treatment area as defined by the design of the channel.

In those embodiments of the device according to the invention which include at least one dispensing unit, the dispensing unit comprises a reservoir for the topical formulation. This reservoir may for instance be provided as a chamber formed between the formulation-impermeable outer layer and rim layer. Such a chamber may for instance be formed by providing an area within the device in which the formulation-impermeable outer layer and rim layer are not adhered to one another, so that a chamber is formed. Alternatively, a separate pouch may be provided interposed between the formulation-impermeable outer layer and the rim layer. Such a pouch may for instance be used if prolonged direct contact between the formulation and the material of the outer and rim layer is to be avoided. In further embodiments of the device according to the invention, the reservoir may take the form of a pouch, an ampule or a tube. As the chamber, pouch, ampule or tube all act as the reservoir for the topical formulation, they must be formed in such a way that a predetermined amount of the topical formulation can be filled into it and that it is possible to release topical formulation therefrom into the channel. This may for instance be achieved by providing an opening or outlet into the channel through which the liquid formulation may flow. Again, this opening may be provided by not providing any adherence between the formulation-impermeable outer layer and rim layer in the area in which the opening connecting the chamber/pouch and the channel is to be formed. Alternatively such an opening or outlet can be formed by providing a tube, for instance a plastic tube, interposed between the formulation-impermeable outer layer and the rim layer in such a manner that a connection is formed between channel and chamber or pouch. In yet further embodiments of the device according to the invention the dispensing unit is pressure-activated, i.e. topical formulation is released into the channel upon exertion of a sufficient amount of pressure onto the reservoir. The amount of pressure required can be controlled via the choice of materials that are used to form the reservoir of the dispensing unit. Usually, the reservoir will be constructed in such a way that the user of the device can release topical formulation from the reservoir by simply exerting pressure on the reservoir with her fingers. For this purpose, the outer surface of the formulation-impermeable outer layer can be marked to clearly indicate the position of the reservoir in the device. In yet further embodiments of the device according to the invention the dispensing unit comprises a pressure-rupturable pouch which acts as the topical formulation containing reservoir. This pouch ruptures upon exertion of a sufficient amount of pressure thereon to release the formulation into the channel. The amount of pressure required to rupture the pouch can again be controlled by the choice of materials from which the pouch is formed. Thin polymeric films that are impermeable to the topical formulation can for instance be used for forming the pouch, e.g. LDPE films with a very thin thickness, for instance of about 1.5 mil or less.

The device according to the invention can be designed to release a single dose of topical formulation into the channel and thereby to the patient or to allow for the release of additional doses. This may be achieved either by providing a sufficiently large reservoir in the device that will hold topical formulation for more than one dose or by providing more than one dispensing unit in the device, i.e. two, three or more dispensing units.

In further embodiments of the device according to the invention, the channel has a lower end facing the back end of the device, said lower end extending in essentially traversal direction and the dispensing unit is positioned adjacent to the lower end of the channel. By positioning the dispensing unit at the lower end of the channel and thereby between the lower end of the channel and the back end of the device, which in use will be a position in the device opposite from the vestibule area, the channel can be positioned to cover those parts of the vulvar showing the highest prevalence of vulvodynia, i.e. the vestibule area.

In yet further embodiments of the device according to the invention the channel has a upper end facing the front end of the device and the width of the channel is increased at least in sections of the channel along its length in direction to the front end compared to the width of the channel at the lower end. The width of the channel can thereby be adapted to best conform to the anatomy of the vulvar area so that delivery of the topical formulation to those areas in need of treatment is maximized.

In some embodiments of the invention, the device comprises at least one undergarment fastener. The undergarment fastener keeps the device in place during use. The undergarment fastener may for instance be a pressure-sensitive adhesive applied to one or more areas of the outer surface of the formulation-impermeable outer layer. The pressure-sensitive adhesive serves to make the device adhere reliably to the inner side of the fabric of the undergarment and prevents the device from shifting its position during use. The pressure-sensitive adhesive allows for the device to be easily removed from the undergarment by simply pulling it off the garment. Suitable pressure-sensitive adhesives are those commonly used as undergarment fasteners on sanitary napkins or panty liners. The nature of the adhesive is not critical, as long as it shows an appropriate level of adhesion on the surface of the material used as the formulation-impermeable outer layer and is acceptable for skin contact, e.g. is biocompatible with the human skin.

In further embodiments of the invention the outer layer of the device comprises a wing area at each of its longitudinal sides, wherein each of said wing areas comprises at least one undergarment fastener. Just as with sanitary napkins, the wing areas during use are folded around the fabric of the undergarment such that the undergarment fasteners can be attached to the outer side of the undergarment fabric. This provides for additional fixation of the device in the desired position during use. Again, the undergarment fasteners can be provided as areas of pressure-sensitive adhesive on the outer surface of the formulation-impermeable outer layer of the device.

In yet further embodiments of the invention the device comprises a removable first release liner fastened to the outer surface of the formulation-impermeable outer layer. The release line protects the garment fastener and is removed from the device prior to use. The material of the release liner can be any material commonly used as release liners in disposable absorbent articles such as sanitary napkins or panty liners or transdermal drug delivery devices. Examples of such release liners are for instance those provided by the company 3M, e.g. 3M Release Liners 4996; 4997; 4986; 4935; 4998; and 7526 or release liners available from Fox River Associates, LLC, such as Fox River Liner S1S; S2S, etc.]

In yet further embodiments of the invention, the device comprises a removable second release liner fastened to the first release liner and covering the skin contact surface of the carrier layer. The second release liner protects the skin contact surface of the topical formulation carrier and is removed from the device prior to use. In some embodiments, the second release liner together with the first release liner may form a pouch in which the device stored prior to use, i.e. the first and second release liner have a larger size than the device and are joined to each other to form a protective pouch. To form such a pouch the first and the second release liner may be made to adhere reliably to each other, e.g. by using pressure sensitive adhesives or the like. The use of the pressure-sensitive adhesive allows the two release liners to be separated from each other by pulling them apart. The same materials that are used to make the first release liner may also be used to make the removable second release liner.

The device according to the present invention is designed for delivery of a topical formulation for treatment of pain affecting the vulvar area of the female human genital organ, especially for treatment of vulvodynia. The topical formulation can be integral part of the device or can form part of a kit comprising the device and the formulation as separated components which are combined prior to use of the device. The topical formulation used in the present invention comprises an active agent, which should have an analgesic desensitizing effect when used topically. Suitable active agents can be selected from the group of VG-sodium channel blockers or new VG sodium channel blockers, such as lidocaine, benzocaine, pramoxine, doxepin, benzydamine, dyclonine, bupivacaine, prilocaine, tetracaine, procaine or cinchocaine; amitriptyline, doxepin, GTX2,3 and GTX1,4 (Gonyautoxins), neosaxitoxin and tetrodoxin; mast cell stabilizers such as nedocromil or cromolyn; non-pungent TRPV-1 agonists such as N-palmitoyl-vanillamide (palvanil), arvanil, olvanil; endogenous cannabinoids and cannabinoids such as palmitoylethanolamide (PEA), anandamide and cannabidiol; gabapentinoids such as gabapentin or pregabalin; potassium channel openers and modulators such as diclofenac, retigabine, flupirtine or cromakalim or baclofen; alpha-2 adrenergic agonists such as clonidine or dexmedetomidine, or NMDA antagonists such as ketamine; or combinations thereof. Additionally, the topical formulation may optionally comprise desensitizing, non-histaminergic alkaline or alkaline earth metal compound, such as potassium or strontium salts. The anions in these salts can either be organic or inorganic anions.

In further embodiments of the present invention, the topical formulation comprises as active agent at least one or more VG-sodium channel blockers or new VG sodium channel blockers.

These can be used alone or in combination with active agents from another drug class, such as mast cell stabilizers and/or desensitizing, non-histaminergic alkaline earth metal salts. For instance, the topical formulation may comprise one or more VG-sodium channel blockers or new VG-sodium channel blockers selected from the group consisting of lidocaine, pramoxine, benzocaine, dyclonine, doxepin, amitriptyline, GTX2,3 and neosaxitoxin. Additionally, the topical formulation may comprise one or more agents selected from the group consisting of cromolyn, nedocromil, palmitoylethanolamide (PEA), cannabidiol, and N-palmitoyl-vanillamide (palvanil). Additionally, the topical formulation may comprise one or more agents selected from the group consisting of strontium, preferably in salt form, gabapentin, diclofenac, baclofen, clonidine and ketamine.

In yet further embodiments the topical formulation comprises at least one voltage gated sodium channel blocker, especially lidocaine, pramoxine and benzocaine, in combination with a mast cell stabilizer, especially cromolyn, and a desensitizing, non-histaminergic alkaline or alkaline earth metal compound, especially potassium or strontium, preferably a strontium salt, e.g. strontium chloride.

The topical formulation must have suitable rheological properties and a suitable viscosity for the intended topical use. These properties might differ, if the topical formulation prior to use of the article is only present as an impregnation on the carrier layer or if the topical formulation is additionally or exclusively present in the dispensing unit. Preferably, the topical formulation is a fluid with a viscosity within the range of 5 to 600 cps as measured by a Brookfield LVT Viscometer #1 Spindle at 60 RPM at 25° C. (77° F.). Additionally, the formulation should be stable at a temperature of 39° C. without separation, flocculation or precipitation. Preferably, the formulation should not leave a rigid or rough surface upon drying to avoid discomfort to the patient. Additionally, the formulation should be pH-balanced for vaginal use, preferably with a pH-value of 3.5 to 4.5.

In a further aspect of the present invention a topical formulation for treatment of pain affecting the vulvar area of the female human genital organ is provided, wherein the topical formulation comprises
a) at least one voltage-gated sodium channel blocker;
b) at least one mast cell stabilizer and/or a skin-desensitizing, non-histaminergic alkaline or alkaline earth metal compound and
c) at least one pharmaceutical carrier or excipient, wherein the topical formulation has a viscosity within the range of 5 to 600 cps as measured by a Brookfield LVT Viscometer #1 Spindle at 60 RPM at 25° C. and a pH-value in the range of 3.5 to 4.5.

In specific embodiments of this aspect of the invention, the topical formulation comprises at least one voltage-gated sodium channel blocker selected from the group consisting of lidocaine, benzocaine, pramoxine, doxepin, benzydamine, dyclonine, bupivacaine, prilocaine, tetracaine, procaine or cinchocaine; amitriptyline, doxepin, GTX2,3 and GTX1,4, neosaxitoxin and tetrodoxin, or combinations thereof. In some embodiments the voltage gated sodium channel blocker is selected from the group consisting of lidocaine, benzocaine and pramoxine.

In embodiments of the topical formulation according to the invention, the mast cell stabilizer is selected from the group consisting of cromolyn and nedocromil and the skin-desensitizing, non-histaminergic alkaline or alkaline earth metal compound is a potassium or strontium salt, preferably, potassium nitrate or strontium chloride.

The amount of topical formulation for use with the device depends of the number of dosages that are to be delivered by the dispensing unit. Preferably, the amount of topical formulation will be in the range of 0.5 to 5 ml, more preferably from 1.0 to 3.0 ml, still more preferably from 1.5 to 2.5 ml.

Besides the active agent, the topical formulation comprises at least one excipient, selected from the group consisting of solvents, e.g. water, benzyl alcohol, ethanol, SD-alcohol 40-B USP (United States Pharmacopeia); lubricants and skin-conditioning agents, such as aloe barbadensis leaf juice (aloe vera), carbomers, glycerin, glyceryl laureate and jojoba oil; topical antiseptics such as benzalconium chloride; preservatives and fungicides, e.g. caprylyl glycol, propylene glycol, methylparaben, and propylparaben; emulsifiers and surfactants, e.g. poloxamer, disodium EDTA, hydroxyethyl cellulose and triethanolamine, and buffering and softening agents, such as sodium hydroxide and monobasic potassium phosphate. Preferably, the topical formulation comprises the active agent in a range of 0.1 to 20 wt-% of the formulation, preferably in the range of 0.5 to 10 wt-%, preferably 1 to 8 wt-%. In some embodiments the formulation comprises 2 to 8 wt-% of at least one voltage gated sodium channel blocker, 1 to 6 wt-% of at least one mast-cell stabilizer, and/or 1 to 6 wt-% of a desensitizing, non-histaminergic alkaline or alkaline earth metal compound.

In some embodiments of the invention, the topical formulation comprises between 40 to 99 wt-%, especially between 50 to 90 wt-%, specifically between 50 to 80 wt-% of at least one solvent. In some embodiments of the invention, the topical formulation comprises between 0.01 to 30 wt-%, especially between 0.01 to 25 wt-% of at least one lubricant and/or skin-conditioning agent. In some embodiments of the invention, the topical formulation comprises between 0.01 to 3%, especially between 0.01 to 1 wt-% of at least one topical antiseptic. In some embodiments of the invention, the topical formulation comprises between 0.01 to 30 wt-%, especially between 0.01 to 20 wt-%, specifically between 0.01 to 10 wt-% of at least one preservative and/or fungicide. In some embodiments of the invention, the topical formulation comprises between 0.01 to 40 wt-%, especially between 1 to 30 wt-%, specifically between 10 to 30 wt-% of at least one emulsifier and/or surfactant. In some embodiments of the invention, the topical formulation comprises between 0.01 to 20 wt-%, especially between 0.1 to 15 wt-%, specifically between 1 to 10 wt-% of at least one buffering and/or softening agent.

In a further aspect of the invention a kit for the topical treatment of pain affecting the vulvar area of the female human genital organ is provided, wherein the kit comprises a device (1) that is a layered article shaped to be placed in use inside a female undergarment and at least partially in skin contact with the female vulvar area said article having a longitudinal direction (L), a transverse direction (T), a front end (F), a back end (B), and two longitudinal sides (S, S'), and said device (1) comprises at least
a) a formulation-impermeable outer layer (2) having an outer surface (2a) and an inner surface (2b);
b) a carrier layer (5) having an inner carrier surface (5a) and a skin-contacting surface (5b), wherein said inner carrier surface (5a) faces in the direction of the inner surface (2a) of the formulation-impermeable outer layer (2);
and wherein
the kit further comprises a topical formulation to be applied to the skin-contacting surface of the carrier layer prior to use of the device, said topical formulation comprising at least one active agent for treating pain affecting the vulvar area of the female human genital organ.

The topical formulations and materials used for the device comprised in the kit correspond to those of the device of the other aspects of the invention described above.

In a further aspect the present invention relates to a method of treating vulvodynia, wherein the method comprises the step of topical application of an active agent to the female vulvar area by means of bringing the skin-contacting surface of the carrier layer of the device according to the invention into skin contact with the female vulvar area. The device may be the device according to those embodiments of the aspects of the invention in which the topical formulation is integral part of the device, i.e. either as an impregnation on the carrier layer of the device and/or is provided in the dispensing unit, or the device may be part of the kit according to the invention.

In the following, the invention will be further described by means of selected examples and with reference to FIGS. 1 to 4. These examples and figures are included for illustrative purposes only and are not to be construed as in any way limiting the scope of the present invention as outlined in the claims.

Figure 1:
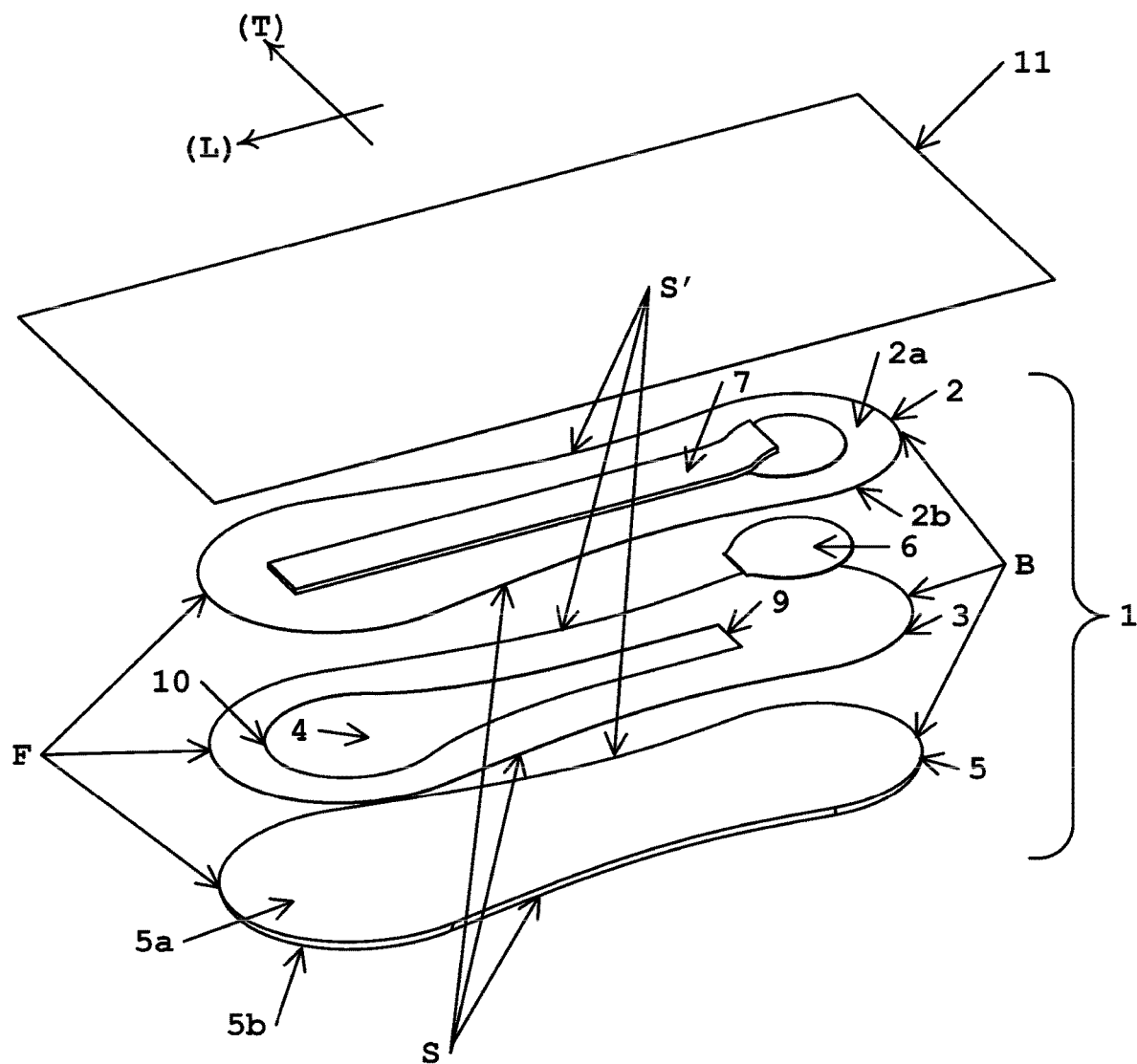
FIG. 1 shows an exploded view of a first embodiment of the device according to the invention.

LIST OF REFERENCE NUMERALS AS USED IN THE FIGURES (1) Device
(L) longitudinal direction of device (1)

Figure 2:
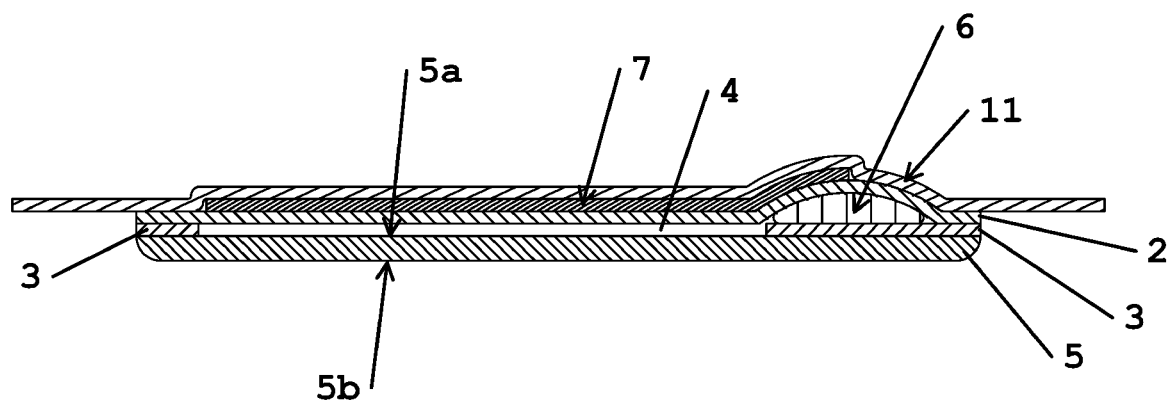
FIG. 2 shows a longitudinal cross sectional cut through the device shown in FIG. 1.

(T) transverse direction of device (1)
(F) front end of device (1)
(B) back end of device (1)
(S, S') longitudinal sides of device (1)
(2) formulation-impermeable outer layer
(2a) outer surface of formulation-impermeable outer layer (2)
(2b) inner surface of formulation-impermeable outer layer (2)
(3) rim layer
(4) channel
(5) carrier layer
(5a) inner carrier surface of carrier layer (5)
(5b) skin-contacting surface of carrier layer (5)
(6) dispensing unit
(7) undergarment fastener
(8) wing area
(9) lower end of channel (4)
(10) upper end of channel (4)
(11) first release liner
(12) second release liner
(13) pressure-sensitive adhesive FIG. 1 shows a first example of the device according to the invention. The device (1) has the form of a conventional panty liner with a longitudinal direction (L) and a transverse direction (T). FIG. 2 shows a view of a cross sectional cut along the longitudinal direction (L) of the device according to the example shown in FIG. 1. The device (1) has a front end (F), a back end (B) and longitudinal sides (S, S'). The device comprises a carrier layer 5 the outer surface of which defines skin-contacting surface (5b). This is the surface of the device which during use will at least partially be brought into skin contact with the user. Overlaying carrier layer (5) on its inner carrier surface (5a), i.e. the surface opposite to skin-contacting surface (5b), is formulation-impermeable rim layer (3). An inner section of the material forming formulation-impermeable rim layer (3) has been cut out to form a channel (4). Overlying formulation-impermeable rim layer (3) is formulation-impermeable outer layer (2), on the outside surface (2a) of which a strip of pressure-sensitive adhesive has been applied to act as a garment fastener (7). Before the device is brought into position for use, garment fastener (7) is protected by a release liner (11), which is removed when the device is made ready for use. Channel (4) in formulation-impermeable rim layer (3) runs in the longitudinal direction and has a lower end (9) facing in the direction of the back end (B) of the device, and an upper end (10) facing in the direction of the front end (F) of the device (1). The width of channel (4) varies such that an essentially circular section is formed near the front end (F) of the device. The form of channel (4) is adapted to the anatomy of the vulvar area so that the vestibule area of the vulvar is covered by the area of carrier layer (5) corresponding to channel (4). Adjacent to lower end (9) of channel (4) in direction of the back end (B) of device (1) lies, interposed between formulation-impermeable rim layer (3) and outer formulation-impermeable layer (2), dispensing unit (6), which in this example is in the form of a pouch made out of a membrane material that can be ruptured by applying pressure on the pouch and that is also impermeable to the formulation. Carrier layer (5), formulation-impermeable rim layer (3), formulation-impermeable outer layer (2) and dispensing unit (6) are adhered to each other, where desired, using conventional methods commonly used e.g. in the art of disposable absorbent articles. Formulation-impermeable outer layer (2) and carrier layer (5) are not adhered to each other in the area defined by channel (4) of rim layer (3) leaving a void space between the two layers thereby forming the channel (4) into which the topical formulation can be released and will be easily distributed therein. Being placed directly adjacent to lower end (9) of channel (4), the pouch forming dispensing unit (6) will rupture in this area and release an amount of the formulation contained therein into the channel (4) when sufficiently high pressure is applied thereon, because this is the section of the pouch which is not or only to a lower degree additionally reinforced by the over- and underlying materials of the formulation impermeable outer layer (2) and rim layer (3). The formulation released by the dispensing unit (6) into channel (4) is distributed therein and is absorbed into carrier layer (5) via the area of inner carrier surface (5a) situated below the channel (4). The topical formulation is transported to the skin-contacting surface (5b) of layer (5) and thereby administered to the treatment area. Because the form of the channel (4) has been adapted to the anatomy of the vulvar area, the topical formulation is efficiently administered to those areas of the vulvar in need of treatment.

The formulation-impermeable outer layer (2) and the formulation-impermeable rim layer (3) can for instance be made of a white LDPE-foil, the carrier layer (5) of a full cotton batting non-woven with a 3 mm thickness. For the dispensing unit, a LDPE foil with a thickness of 1.5 mil or less can be used. The device can be assembled by die-cutting the different layers from sheets of the respective materials and adhering them to each other using conventional adhesive technologies commonly used in the art of disposable personal hygiene articles, such as sanitary napkins and panty liners. The prefabricated and filled pouch can be adhered in between the formulation-impermeable outer layer and the rim layer.

Figure 3:
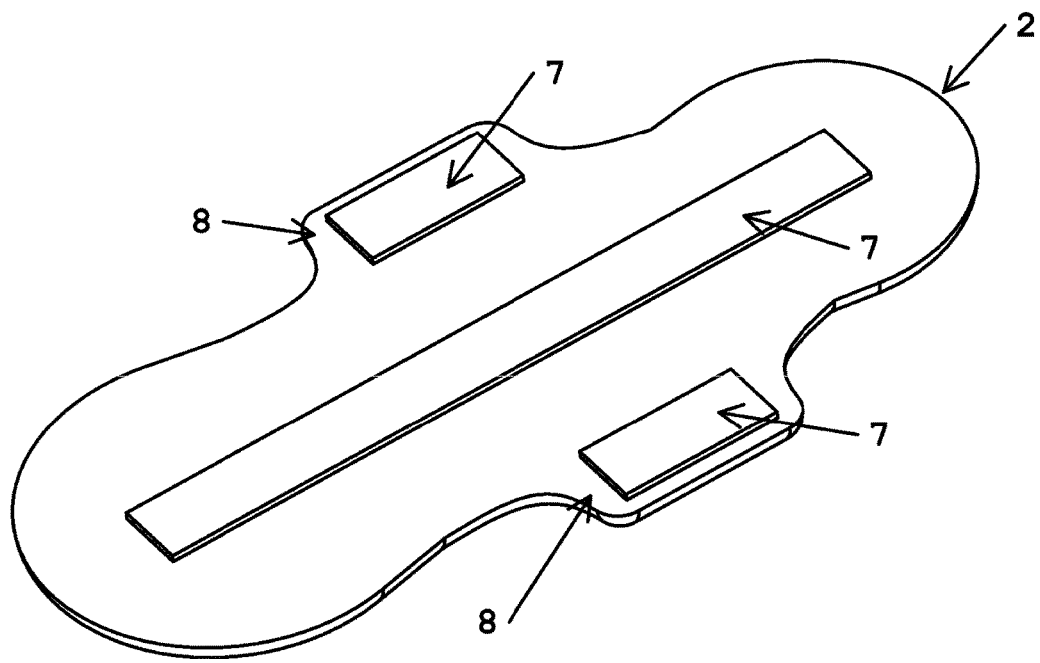
FIG. 3 shows an alternative design for a formulation-impermeable outer layer (2) with wing areas at each of its longitudinal sides.

FIG. 3 shows an alternative design for a formulation-impermeable outer layer (2) for use in a device according to the invention. The outer layer (2) additionally comprises a wing area (8) at each of its longitudinal sides (S, S'). These wing areas (8) each comprise an additional strip of pressure-sensitive adhesive on the outside surface thereof, which also act as garment fasteners (7). When the device is placed inside the undergarment of the patient for use, the garment fastener (7) located centrally on the outside surface (2a) of the outer layer (2) is adhered to the inside of the undergarment. The wing areas are then folded around the undergarment at the leg openings and adhered to the outside of the undergarment via the garment fasteners (7) located on the wing areas (8) to provide additional support in keeping device (1) in the predetermined position of the undergarment during use.

Figure 4:
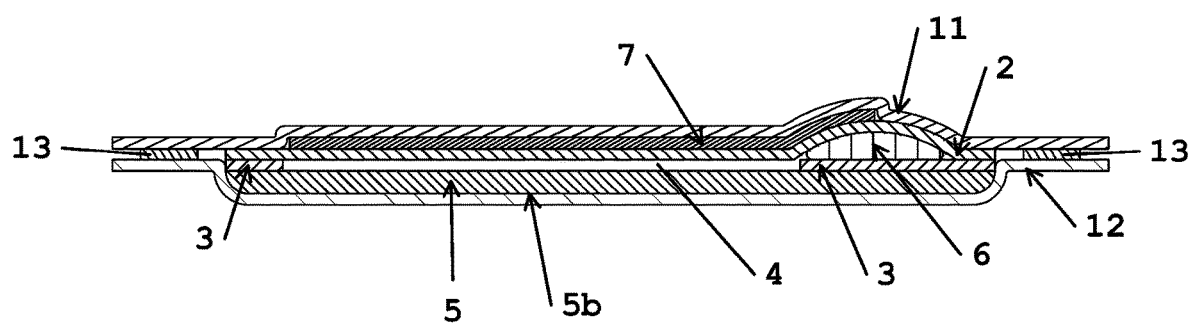
FIG. 4 show a longitudinal cross sectional cut through another embodiment of the inventive device comprising a second release liner.

FIG. 4 shows a cross sectional view along a longitudinal cut of a second example of a device according to the invention. The device according to this example is essentially identical with the previous example but comprises an additional second release liner (12) which protects the skin-contacting surface (5b) of the carrier layer (5) when the device is not in use. The second release liner is releasably adhered to the first release liner using a pressure-sensitive adhesive (13), whereby the two release liners (11, 12) form a protective pouch for those parts of the device which in use are placed inside the undergarment of the user.

Example 1 a) A 28 year old white female had complained of an 18 month history of vulvar pain. She described a generalized stinging sharp pain localized in her labia and vestibule and usually triggered by touch, contact with tights garments, and sexual intercourse. She also complained of a sensation of hypersensitivity to touch in the anterior vestibule. On an average, she rated her overall vulvar pain at 6-7 on the numerical pain scale 0-10, where 10 corresponds to the worst pain imaginable and 0 to no pain.

Gynecological evaluations and imaging studies, including an MRI of the pelvis were unrevealing for any specific etiology, such as infections, dermatological inflammatory conditions and structural pelvic pathologies. She was diagnosed as having vulvodynia. Multiple trials of treatments, including: 1) oral drugs such as tricyclic antidepressants, gabapentin, pregabalin, duloxetine; 2) a variety of OTC creams, 3) pudendal nerve blocks provided either intolerable side effects and/or no significant benefit.

She reported some mild relief (about 25%) of short duration (about 20 minutes) from the application of a cotton ball soaked in a compounded preparation of liquid lidocaine. She was however reluctant to use the cotton ball remedy. First, because the application of liquid lidocaine was followed by a local burning sensation lasting for about 3-5 minutes before any noticeable pain relief could occur. Secondly, it was awkward for her to apply the cotton ball multiple times during daily activities. She then received a set of pads, in the form of feminine sanitary pads. A compounded gel with 4 g lidocaine, 4 g cromolyn and 0.2 g Aloe Vera, 0.05 g methylparaben NF, 0.253 g propyleneparaben NF and purified water, USP, q.s. per 100 ml gel, was applied to each pad. She tried the pads and she kept each pad for a few hours. She reported improved benefit over time. The relief was more noticeable at the time a fresh pad was applied. Overall she reported 75% pain relief and no irritation of discomfort from the pad use.

b) A 32 year old white female had complained of more than 12 month history of vulvar pain. She was also known to suffer from anal fissures and ulcerative colitis. She described her vulvar pain as constant and burning. She complained of hypersensitivity associated to a sensation of rawness localized in her vestibule. The pain was made worse by sexual intercourse. She underwent multiple medical evaluations. No specific causes of her vestibular pain were identified. On an average, she rated her overall vulvar pain at 8-9 on the numerical pain scale 0-10, where 0 is no pain and 10 the worst pain imaginable. Her pain failed to respond to antidepressants, anticonvulsants, pelvic floor muscle therapy. Application of cotton balls soaked in liquid lidocaine caused an intolerable burning sensation in the vulvar region and then only short-lasting mild relief. She received a set of pads, in the form of feminine sanitary pads along with a compounded gel, pH balanced for vaginal use (pH between 3.5-4.5), containing per 100 ml gel benzocaine 4 g, pramoxine 1 g, strontium chloride 2.6 g and poloxamer 407 30 g, methylparaben 0.05 g, propylparaben 0.253 g, EDTA 0.03 g and purified water, USP, q.s. She tried the combination of pad and gel and she was happy to report satisfactory long lasting benefit. She experienced some local numbness, but the pad application did not cause burning or intolerable side effects. Overall she reported more than 50% pain relief.

The invention claimed is:

1. A device for the topical treatment of pain affecting the vulvar area of the female human genital organ, wherein the device is a layered article shaped to be placed in use inside a female undergarment and at least partially in skin contact with the female vulvar area, said article having a longitudinal direction, a transverse direction, a front end, a back end, and two longitudinal sides, and said device comprises at least:

a) a formulation-impermeable outer layer having an outer surface and an inner surface;

b) a formulation-impermeable rim layer, wherein said formulation-impermeable rim layer is superimposed on the inner surface of the formulation-impermeable outer layer and does not cover an inner section thereof thereby defining a channel extending in the longitudinal direction of the article;

c) a carrier layer having an inner carrier surface and a skin-contacting surface, said carrier layer being superimposed on the formulation-impermeable rim layer and the channel such that the inner carrier surface faces in a direction of the formulation-impermeable rim layer and the channel;

d) a topical formulation comprising at least one active agent for treating pain affecting the vulvar area of the female human genital organ;

wherein the carrier layer is at least partially impregnated with the topical formulation and/or at least one dispensing unit is positioned interposed between the formulation-impermeable outer layer and the formulation-impermeable rim layer adjacent to the channel and said dispensing unit contains a topical formulation to be released into the channel.

2. A method of treating vulvodynia, wherein the method comprises the step of topically applying an active agent to the female vulvar area with the device according to claim 1.

3. The device according to claim 1, wherein the channel has a lower end facing the back end of the device and extending in essentially traversal direction, and the dispensing unit is positioned adjacent to a lower end of the channel.

4. The device according to claim 1, wherein the dispensing unit is pressure-activated.

5. The device according to claim 1, wherein the dispensing unit comprises a reservoir comprising topical formulation contained in a rupturable pouch.

6. The device according to claim 1, wherein the channel has an upper end facing the front end of the device and the width of the channel is increased at least in sections of the channel along its length in a direction towards the front end compared to the width of the channel at the lower end.

* * * * *